United States Patent [19]

Passoni et al.

[11] 4,259,332
[45] Mar. 31, 1981

[54] NOVEL TAURINE DERIVATIVES

[75] Inventors: Raffaele Passoni, Milan; Vittorio Camboni, Cigni-Brugherio, both of Italy

[73] Assignee: Laboratorio Chimico Farmaceutico CAUSYTH S.p.A., Milan, Italy

[21] Appl. No.: 120,063

[22] Filed: Feb. 11, 1980

Related U.S. Application Data

[63] Continuation-in-part of Ser. No. 47,040, Jun. 11, 1979, abandoned.

[30] Foreign Application Priority Data

Dec. 7, 1979 [IT] Italy .................................. 28020 A79

[51] Int. Cl.[3] .................. A61K 31/24; A61K 31/325; A61K 31/455; C07C 69/86
[52] U.S. Cl. ..................................... 424/230; 424/266; 424/308; 424/309; 546/318; 560/64; 560/66
[58] Field of Search ................... 546/318; 560/64, 66, 560/74; 424/230, 308, 309, 266; 260/509

[56] References Cited

FOREIGN PATENT DOCUMENTS 1151149 7/1963 Fed. Rep. of Germany ............ 260/457

OTHER PUBLICATIONS

Derwent Belgian Patents Report 95B, Section 5 General Organic, p. 6, Feb. 1, 1963, (Abst. of Belgian Pat. No. 617,781).
Seventh Collective Index, vols. 56–65, p. 22,285S, American Chemical Society, copyrighted 1970, (under Taurine-).
Goldberg et al., Chem. Abstracts, vol. 40, col. 4436[8] (1946).
Goldberg et al., Chem. Abstracts, vol. 41, col. 6900[e] (1947), (abst. of Brit. Pat. 586,453).
Distler et al., Chem. Abstracts, vol. 59. col. 511[d] (19), (abst. of Belg. Pat. No. 617,781, not available).
Seperic, Chem. Abstracts, vol. 82, abst. 64490k, (1975), (abst. of Ger. Offen. 2,406,366).

Primary Examiner—John D. Randolph
Attorney, Agent, or Firm—Buchnam and Archer

[57] ABSTRACT

Novel taurine derivatives of general formula (I)

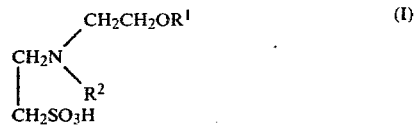

(wherein $R^1$ is nicotinoyl, 3,4,5-trimethoxybenzoyl or acetylsalicyloyl and $R^2$ is as defined for $R^1$ or is —$CH_2CH_2OR^1$) have antilipemic and choleretic activities. The compound in which $R^2$=—$CH_2CH_2OR^1$ and $R^1$ is acetylsalicyloyl exhibits high antiinflammatory, analgesic and antipyretic activity and is essentially free of the unfavorable effect of acetylsalicylic acid on the stomach.

8 Claims, No Drawings

NOVEL TAURINE DERIVATIVES

This application is a Continuation-In-Part of U.S. Ser. No. 047,040 filed June 11, 1979, now abandoned.

The present invention relates to taurine derivatives. More particularly it relates to taurine derivatives which have antilipemic and choleretic activities, antiinflammatory, analgesic and antipyretic activity, to processes for the preparation of such derivatives, and to pharmaceutical compositions of such derivatives.

Taurine, otherwise known as 2-aminoethanesulphonic acid, is a naturally occurring compound of the formula (X).

In particular, it occurs in the human body as a conjugate with bile acids, the conjugate with cholic acid being taurocholic acid.

The present invention provides taurine derivatives of the general formula (I)

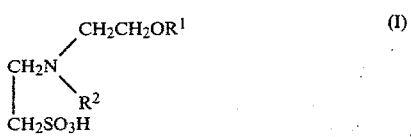

(wherein $R^1$ is a nicotinoyl, 3,4,5-trimethoxybenzoyl or acetylsalicyloyl group, and $R^2$ is as defined for $R^1$ or is a —$CH_2CH_2OR^1$ group wherein $R^1$ is as defined) and pharmaceutically acceptable salts thereof.

The present taurine derivatives have various pharmacological utilities, especially antilipemic and choleretic activities, antipyretic, analgesic and antiinflammatory activity.

Accordingly the present invention provides pharmaceutical compositions which contain a taurine derivative of general formula (I), or a pharmaceutically acceptable salt thereof, together with a pharmaceutically acceptable carrier or diluent. The carrier or diluent can be conventional and the composition may contain further components if desired.

PHARMACOLOGICAL ACTIVITY

The pharmacological activity of the present derivatives is illustrated by the following results for typical derivatives of the invention.

(A) N-nicotinoyl-N-(2-nicotinoyloxy)ethyltaurine, Compound A Toxicology

Mice of either sex were treated orally for 180 days with 200 mg/kg of compound A. There was no mortality nor any significant variation in the weight increase curve when compared with control mice.

Vasodilative activity

The vasodilatory activity of the Compound A of the invention was investigated in comparison with (i) a mixture of the components of Compound A, i.e. N-hydroxyethyltaurine plus nicotinic acid, (ii) nicotinic acid, (iii) mesoinosital hexanicotinate (inositol niacinate), and (iv) 3-pyridylcarbinol tartrate.

The vasodilative activity was evaluated by administering the products endoperitoneally at the doses indicated in Table 1. The test was as described for the vasodilation of the ocular conjunctiva in guinea pigs (J. Pharmacol. 21, 192-1969).

Each value of Table 1 is the average of 10 measurements.

TABLE 1

| | Vasodilator Activity | | | |
|---|---|---|---|---|
| | | | Effect | |
| Compound | Dose (mg/kg) | Positive response (%) | Time of appearance (seconds) | Duration (minutes) |
| A | 0.1 | 0 | 0 | 0 |
| | 1.0 | 80 | 90 | 120 |
| | 10.0 | 100 | 96 | 120 |
| N-hydroxy-ethyltauri-ne + nico-tinic acid | 10.0 | 0 | 0 | 0 |
| Nicotinic acid | 10.0 | 0 | 0 | 0 |
| | 25.0 | 20 | — | — |
| | 50.0 | 80 | 180 | 97 |
| Mesoinosital hexanicotina-te | 1.0 | 0 | 0 | 0 |
| | 10.0 | 100 | 81 | 87 |
| 3-Pyridyl-carbinol tartrate | 0.1 | 0 | 0 | 0 |
| | 1.0 | 40 | — | — |
| | 10.0 | 100 | 57 | 120 |

The results show that the Compound A of the invention possesses a better activity than the 3-pyridylcarbinol compound, both in terms of the number of responses and in terms of the duration. It should be noted that the mixture of N-hydroxyethyltaurine and nicotinic acid possesses no activity, thus showing different pharmacokinetics.

Choleretic activity

The activity of the Compound A of the invention was evaluated in comparison with the activity of (i) N-hydroxyethyltaurine, (ii) nicotinic acid, (iii) a mixture of these two compounds (i) and (ii), and (iv) α-(1-hydroxy-4-phenylcyclohexyl)butyric acid (fencibutirol), which is a known hepatoprotector.

Rats were fitted with a cannula, the bile volume was measured after the first hour, they were then treated with a test compound and the bile volume was measure after the second hour, so as to determine the percentage change. The various compounds were administered intravenously at a dose of 100 mg/kg.

The results are shown in Table 2.

TABLE 2

| | Choleretic Activity | | | | | |
|---|---|---|---|---|---|---|
| | Bile volume ml/h | | | Dry residue mg/h | | |
| Compound | after 1 h | after 2 h | Change % | after 1 h | after 2 h | Change % |
| A | 0.75 | 1.14 | +52.0 | 25.7 | 35.3 | +40.0 |
| N-hydro-xyethyl-taurine | 0.82 | 0.72 | −12.2 | 29.1 | 26.0 | −10.9 |
| Nicoti-nic acid | 0.57 | 0.54 | −5.3 | 21.7 | 20.6 | −5.7 |
| N-hydro-xyethyl-taurine + nicotinic acid | 0.83 | 0.88 | +6.0 | 30.0 | 29.1 | −4.2 |
| α-(1-hy-droxy-4-phenylcy- | | | | | | |

TABLE 2-continued

| | Choleretic Activity | | | | | |
|---|---|---|---|---|---|---|
| | Bile | volume ml/h | | Dry residue mg/h | | |
| Compound | after 1 h | after 2 h | Change % | after 1 h | after 2 h | Change % |
| clohexyl) butyric acid | 0.60 | 1.14 | +90.0 | 23.5 | 32.7 | +39.1 |

Table 2 emphasizes the appearance of choleretic activity of the compound A of this invention, this activity being practically absent in the individual components and in the simple mixture when administered at the same doses.

In comparison with α-(1-hydroxy-4-phenylcyclohexyl)butiryc acid there is a smaller increase in bile volume but an equal increase in the dry residue, which suggests that the product is not hydrocholeretic but truly choleretic.

Again, the pharmacokinetics of the Compound A of the invention are different from those of the components.

Protection against hepatic intoxication by $CCl_4$ and cold

Oral administration of 5 ml/kg of a 20% solution of $CCl_4$ in oil was followed by exposure for 5 hours to a temperature of 4° C. 500 Mg/kg of the Compound A of the invention were administered simultaneously with the $CCl_4$. The BSF was tested in the blood. An average of 20 animals were used per group, and relative to the controls there was a reduction of 16%.

Antilipemic action

Wistar rats were treated for 50 days with a Morris diet or a Handler diet. Simultaneously with the diet they received 200 mg/kg of Compound A or of choline orally every day. The controls only received the diet. The following were examined at the end of the treatment: (a) total cholesterol, total lipids and beta-lipoproteins in the serum, (b) BSF excretion in the bile.

The results indicated in Table 3 are expressed as a percentage change with respect to the controls, each value being the average for 10 animals.

TABLE 3

| | Antilipemic Action | | | |
|---|---|---|---|---|
| | Morris diet | | Handler diet | |
| Parameter | Compound A | Choline | Compound A | Choline |
| (a) Serum | | | | |
| Total cholesterol | −14.3 | −22.9 | −26.9 | −21.1 |
| Total lipids | −17.0 | +2.3 | −19.6 | +44.2 |
| Beta-lipoproteins | −34.3 | +89.8 | −28.9 | — |
| (b) Bile | | | | |
| BSF | +23.5 | −2.8 | +36.0 | −39.5 |

The antilipemic action with the diets used is apparent, thus indicating inter alia a good oral absorption.

Pharmacokinetics

It is possible to make reliable deductions from the pharmacological tests.

(1) The tests under the diets show that the Compound A is absorbed orally, as it acts both on the lipid fractions of the serum and on the BSF bile excretion.

(2) The choleretic activity after intravenous administration shows a clear difference between the activity of the Compound A and the activity of the individual components, and of the simple mixture of these in the stoichiometric proportions in which they exist in the Compound A.

Neither the components nor the mixture have any choleretic action, whereas it appears clearly in the product. It is apparent that if the product had hydrolysed immediately into its components, such activity would have been zero.

This enables it to be stated that if fission were to take place, it would take place at a level such as to modify the pharmacological profile.

(3) The vasodilative action on endoperitoneal administration shows a distinct difference between the Compound A and nicotinic acid.

(a) At 10 mg/kg Compound A gives 100% positive response, whereas nicotinic acid gives 0% at 10 mg/kg and 80% only at 50 mg/kg.

(b) The appearance time is also different. Nicotinic acid has an appearance time which is double that for Compound A.

(c) The duration of activity is also different. Compound A has a duration of 120 minutes at 1 mg/kg, nicotinic acid 87 minutes at 50 mg/kg.

It is apparent that if the activity of Compound A had been due to the immediate liberation of nicotinic acid, these differences could not have been observed.

It can therefore be concluded that the behaviour of Compound A of the invention differs distinctly from the behaviour of the components, for the different administration paths.

(B) N,N-di-[2-(3,4,5-trimethoxybenzoyloxy)ethyl]-taurine (COMPOUND B)

Toxicology

Mice of either sex were treated orally for 180 days with 200 mg/kg of Compound B. No mortality occurred, nor any significant changes in the weight increase curve in comparison with the controls.

Protection against hepatic intoxication by $CCl_4$ and cold

Oral administration of 5 ml/kg of a 20% solution of $CCl_4$ in oil, with simultaneous endoperitoneal administration of 500 mg/kg of Compound B, was followed by exposure for 5 hours at 4° C. BSF in the blood (30 mg/kg i.v.) was tested. A comparison product, homocysteinethiolactone (OCT) was employed.

10 Animals were treated per group, and the results expressed as percentage change with respect to the controls were as shown in Table 4.

TABLE 4

| Hepatic intoxication protection | | |
|---|---|---|
| Test number | Compound | Protection |
| 1 | A | −27.5 |
| | OCT | −22.7 |
| 2 | A | −17.0 |
| | OCT | −18.5 |

BSF bile excretion age change with respect to the control are shown in Table 6.

TABLE 6

| Parameter | CCl4 intoxication cure |||||
|---|---|---|---|---|---|
| | Handler diet || Nath diet || Morris diet |
| | Compound B | Compound B | Choline | Compound B | Compound B | Choline |
| (a) Serum Total cholesterol | −6.3 | −7.3 | −21.1 | −35.2 | −23.2 | −22.9 |
| Total lipids | −15.9 | +9.1 | +44.2 | −20.6 | −22.4 | +2.3 |
| Beta-lipo-proteins | — | — | — | −29.7 | −23.7 | +89.8 |
| (b) Liver Total lipids | −37.7 | −29.1 | −29.2 | −23.4 | −11.5 | +14.0 |
| Fresh organic weight | −24.9 | −13.3 | — | — | — | — |
| (c) Bile:BSF | — | +23.4 | −39.5 | — | +23.8 | −2.8 |

Endoperitoneal administration to rats of 100 mg/kg of Compound B for 4 days was followed on the fourth day, one hour after the last administration, with the rats receiving 10 ml/kg orally of a 10% solution of CCl4 in oil. BSF (5 mg/kg) in the bile was tested.

10 Animals were used per group, and the results expressed as percentage of excretion are shown in Table 5.

TABLE 5

| | BSF bile excretion ||
|---|---|---|
| | Excretion ||
| Animal Group | 30 min. | 60 min. |
| Control | 56.6 | 66.0 |
| CCl4 | 33.1 | 43.9 |
| CCl4 + cpd A | 44.1 | 50.9 |

Curative effect on intoxication by CCl4

Oral administration to rats of 10 ml/kg of a 10% solution of CCl4 in oil was followed with endoperitoneal administration of 100 mg/kg of Compound B after 1 hour. BSF (50 mg/kg i.v.) in the blood was tested after 4 hours. 5 Animals were used per group, and expressed as percentage change with respect to the control, the Compound B gave a reduction of −34.2.

Intoxication by CCl4 and curative treatment

On the first day there was oral administration of 10 ml/kg of a 10% solution of CCl4 in oil and simultaneous endoperitoneal administration of 100 mg/kg of Compound B. On the second and third days, there was endoperitoneal administration of 100 mg/kg of Compound B, then testing of BSF (50 mg/kg i.v.) in the blood.

5 Animals were used per group, and expressed as pecentage variation with respect to the control, there was a reduction by Compound B of 16.1.

Antilipemic action

Wistar rats were treated for 45 days with a Morris diet, a Handler diet or a Nath diet. Simultaneously with the diet they received each day 200 mg/kg of Compound B or choline (except for the Nath diet) orally. The controls received only the diet. 10 Animals were used per group, and the results expressed as a percent- The antilipemic action with the diets used is apparent, indicating inter alia a good oral absorption.

Pharmacokinetics

Deductions can be made from the pharmacological tests.

The tests conducted with the various types of diet, administering Compound B of the invention orally, show an evident action on the parameters considered, which obviously suggests good oral absorption. This might be an optimum by administering the compound in powder form with the diet as in the experiments, or possibly it could be improved by administration in solution.

PREPARATION OF THE TAURINE DERIVATIVES

The invention also provides processes for preparing taurine derivatives of formula (I) and their salts.

One of these processes consists in treating monoethanoltaurine (II) or diethanoltaurine (III) with an activated derivative (IV) (e.g. halide, ester, mixed anhydride) of nicotinic, 3,4,5-trimethoxybenzoic or acetylsalicylic acid, in accordance with the following reaction scheme:

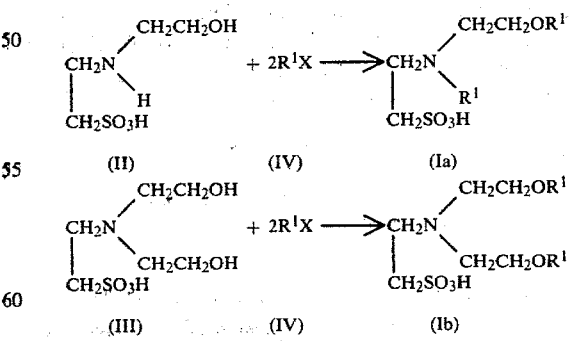

where $R^1$ is as defined, whereas X represents the activating residue, e.g. a halogen atom (normally chlorine), an alkoxy residue (methoxy, ethoxy), or an alkoxycarbonyloxy residue (normally a —OCOOC2H5 residue).

Such reactions according to the invention can be carried out under the conditions generally adopted for the acylation of compounds of alcoholic and/or amino character. Thus, in the most frequent case in which X represents a chlorine atom, acylation is carried out in the presence of a tertiary base, such as triethylamine or pyridine.

According to a further preparative process, a compound of formula (V) is reacted with the hydrochloride (or another salt) of a -acyloxyethylamine of general formula (VI), in the presence of an acid acceptor, such as sodium ethoxide. The intermediate (VII) thus obtained can then be acylated e.g. under nitrogen with an activated derivative (IV). Likewise, compounds of formula (V) can be reacted with a hydrochloride (or another salt) of a di-(β-acyloxy)ethylamine (VIII) in the presence of an acid acceptor, for example sodium ethoxide. The process is illustrated by the following reaction scheme:

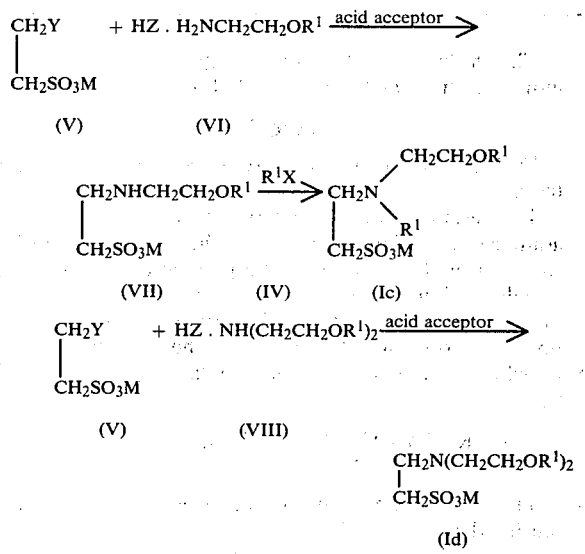

wherein $R^1$ and X are as previously defined, Y is a leaving group, for example chlorine, bromine, O-tosyl, etc, Z is an anion, usually chloride, and M is a cation, usually sodium.

The taurine derivatives of general formula (I) can also be obtained by reacting the sodium of other salt of taurine with a compound of general formula (IX), in accordance with the scheme:

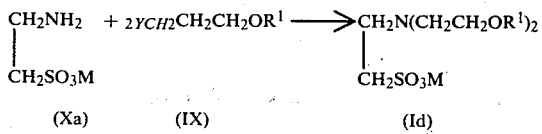

where $R^1$, X, Y and M are as previously defined.

The salts such as the compounds of formula(Ic) or (Id) can readily be converted by conventional methods to the corresponding acid, i.e. a taurine derivative of general formula (I). Equally the acids can be converted to salts if so desired.

The present invention is further illustrated by the following non-limiting examples.

EXAMPLE 1

N-nicotinoyl-N-(2-nicotinoyloxy)ethyltaurine (a) N-(2-hydroxy)ethyltaurine

A solution in 2 liters of water of 315 g of sodium bromoethanesulphonate (Organic Synthesis, Coll. Vol. II, p. 558) and 450 g of ethanolamine was heated to 60°–70° C. for 30 minutes. Excess ethanolamine and water were then distilled off under vacuum, and the residue dissolved in 250–270 ml of water. 2.2 Liters of concentrated hydrochloric acid was added and the solution kept in a refrigerator for 15–20 hours. The precipitated sodium chloride was filtered off using a filter pump, and the solution concentrated until a viscous oil was obtained. The oil was diluted with 60 ml of water and ethanol (about 500 ml) then added to precipitate the reaction product. After the mixture has been left one night in a refrigerator, precipitation was almost complete. The product obtained was filtered off with a filter pump. About 130–140 g of crystalline product was obtained, having a melting point of 180°–183° C.

Elementary analysis for $C_4H_{11}O_4NS$: Calculated %: C=28.40; H=6.60 Found %: C=28.70; H=6.70.

(b) N-nicotinoyl-N-(2-nicotinoyloxy)ethyltaurine

35 G of N-(2-hydroxy)ethyltaurine obtained as above was placed in 100 ml of pyridine. 75 G of finely powered nicotinoyl chloride hydrochloride was then slowly added under agitation. The temperature rose spontaneously, but was not allowed to exceed 80°–85° C. When the temperature began to fall, the solution was heated for one hour at 80°–85° C., and then cooled. The viscous solution was diluted with 100 ml of ethanol, adjusted to a pH of 3.5 by adding concentrated hydrochloric acid, a further 500 ml of ethanol added and the solution then left to stand in a refrigerator. The required product was filtered off with a filter pump after 24 hours. About 50 g of N-nicotinoyl-N-(2-nicotinoyloxy)ethyltaurine was obtained, having a melting point of 175°–176° C. The product was purified by dissolving in a minimum quantity of water and reprecipitating with ethanol.

Elementary analysis for $C_{16}H_{17}O_6N_3S$: Calculated %: C=50.65; H=4.52 Found %: C=50.82; H=4.48.

Infrared spectroscopy and nuclear magnetic resonance date further confirmed the identity of the product obtained.

EXAMPLE 2

N,N-di-[2-(3,4,5-trimethoxybenzoyloxy)ethyl]taurine (a) N,N-di[(2-hydroxy)ethyl]taurine A solution of 90 g of sodium bromoethanesulphonate (Organic Synthesis, Coll. Vol. II, p; 558) and 110 g of ethanolamine in 1500 ml of water was heated over a steam bath for about 2 hours and the reaction mixture left to stand for one night. The excess diethanolamine and water were then distilled off under vacuum, and the residue taken up in 100 ml of water and 800 ml of concentrated hydrochloric acid. The solution was cooled and filtered from the sodium chloride by a filter pump. It was then concentrated under vacuum until an oil was obtained which was taken up in boiling ethanol. On cooling, a crystalline product was obtained having a melting point of 163°–165° C., which was recrystallised from ethanol and water. 16 G of product were obtained, the analytical and spectroscopic data of which confirmed the identity of the product as the compound (III).

(b) N,N-di-[2-(3,4,5-trimethoxybenzoyloxy)ethyl]taurine 8.5 G of the product obtained in Example 2 (a) was suspended in 25 ml of anhydrous pyridine, and 18.4 g of 3,4,5-trimethoxybenzoyl chloride added slowly under agitation. After being left for one hour at ambient temperature the mixture was heated to 80° C. for a further hour. It was then cooled to ambient temperature, diluted with 50 ml of ethanol and left to stand in a refrigerator. A colourless crystalline compound precipitated which milted at 174°–178° C. After recrystallisation from methanol, the melting point was 180°–183° C. The yield was 11.5 g of pure product.

Elementary analysis for $C_{26}H_{35}O_{13}NS$: Calculated %: C=51.91; H=5.82; N=2.32. Found %: C=52.07; H=5.88; N=2.26.

EXAMPLE 3

N-nicotinoyl-N-(2-nicotinoyloxy)ethyltaurine

A solution of 200 g of the sodium salt of taurine, 90 g of barium hydroxide and 70 g of ethylene oxide in 900 ml of water was kept for 96 hours at 10° C., after which all the barium was precipitated with $H_2SO_4$ and filtered off. The solution was concentrated under reduced pressure to about 200 ml and 1.8 liters of concentrated hydrochloric acid adde, the precipitated sodium chloride filtered off, and the solution evaporated under reduced pressure until it was of syrupy consistency. By adding ethyl alcohol a precipitate was obtained having a melting point of 180°–183° C. and whose analysis and spectra were identical with those of the product obtained in Example 1 (a).

By treating this product as described in Example 1 (b), N-nicotinoyl-N-(2-nicotinoyloxy)ethyltaurine was obtained, having a m.p. of 175°–176° C. and whose analysis and spectra were identical with those of the product obtained in Example 1 (b).

EXAMPLE 4

N,N-di-[2-(3,4,5-trimethoxybenzoyloxy)ethyl]taurine

A solution of 12 g of the sodium salt of taurine, 10 g of bariumhydroxide and 8 g of ethylene oxide in 100 ml of water was kept for 96 hours at 10° C., after which barium was precipitated with $H_2SO_4$ and filtered off. The solution was concentrated under reduced pressure to about 50 ml, about 1 liter of concentrated hydrochloric acid was added, the precipitate formed was filtered off and the solution evaporated under reduced pressure to a syrupy consistency. It was taken up in boiling ethanol, cooled and the precipitate obtained was filtered off and recrystallised from 80% ethanol, to give a product of m.p. 163°–165° C. identical with the product obtained in Example 2 (a).

By treating this product as described in Example 2 (b), N,N-di-[2-(3,4,5-trimethoxybenzoyloxy)ethyl]taurine was obtained, m.p. 178°–182° C., identical with that obtained in Example 2 (b).

EXAMPLE 5

N-(nicotinoyl)-N-(2-nicotinoyloxy)ethyltaurine

A mixture of 98 g of cholamine hydrochloride, 2 liters of dimethoxyethane and 180 g of nicotinoyl chloride hydrochloride was left at ambient temperature for one night under agitation. The excess HCl was removed with a current of nitrogen, the solution then evaporated at reduced pressure and redissolved in 3 liters of anhydrous ethyl alcohol. 140 G of sodium ethoxide in 1 liter of absolute alcohol, followed by 210 g of sodium bromoethanesulphonate, was then added. 170 G of KI were then added and the mixture left at ambient temperature for 120 h.

The resultant mixture was evaporated under reduced pressure, 750 ml of pyridine added, and then 180 g of nicotinoyl chloride hydrochloride, this latter slowly under agitation, while cooling the mass so that the temperature did not exceed 80° C. It was heated for 1.5 hours, then cooled, diluted with 0.5 liters of ethanol, acidified with concentrated HCl to a pH of 3.5 and a further 2.5 liters of ethanol then added. The product, which had a m.p. of 174°–176° C., was filtered off, and was identical to the N-nicotinoyl-N-(2-nicotinoyloxy)ethyltaurine obtained in Example 1.

EXAMPLE 6

N,N-di-[2-(3,4,5-trimethoxybenzoyloxy)ethyl]taurine

A mixture of 14 g of diethanolamine hydrochloride, 200 ml of dimethoxyethane and 47 g of 3,4,5-trimethoxybenzoyl chloride was left at ambient temperature for one night under agitation. The excess HCl was removed with a current of nitrogen, and the solution then evaporated under reduced pressure and taken up in 300 ml of anhydrous ethyl alcohol. 14 G of sodium ethoxide in 200 ml of absolute alcohol was added under cooling, then 21 g of sodium bromoethanesulphonate and 1.7 g of potassium iodide. After 120 hours at ambient temperature, the inorganic salts were filtered off and the solution concentrated under reduced pressure to a small volume.

The mixture was then left to stand for one night, then filtered and crystallised from methanol. The product had a melting point of 179°–182° C. and was identical to that obtained in Example 2.

EXAMPLE 7

N-(nicotinoyl)-N-(2-nicotinoyloxy)ethyltaurine

180 G of nicotinoyl chloride hydrochloride was added in small portions at a temperature of 0° C. to 544 g of ethylene oxide in 200 ml of carbon tetrachloride. The mixture was left under agitation for 6 hours, after which the solvent was evaporated at reduced pressure, and the solution taken up in 1 liter of dimethoxyethane. 150 G of the sodium salt of taurine and 1.5 g of potassium iodide were added, after which the mixture was left under agitation for 96 hours at ambient temperature. The mixture was then evaporated under reduced pressure, 750 ml of pyridine added slowly under agitation, followed by 180 g of nicotinoyl chloride hydrochloride in small portions. The mixture was heated to 80° C. for 2 hours, cooled, 0.5 liters of ethanol added, the mixture acidified with concentrated HCl to a pH of 3.5 and a further 2.5 liters of ethanol then added. After some hours of standing, the precipitated product was filtered off. The product had a m.p. of 175°–176° C., and was identical with the product obtained in Example 1.

EXAMPLE 8

N,N-di-[2-(3,4,5-trimethoxybenzoyloxy)ethyl]taurine

180 G of nicotinoyl chloride hydrochloride was added in small portions at a temperature of 0° C. to 44 g of ethylene oxide in 200 ml of carbon tetrachloride. The mixture was left under agitation for 6 hours, after which the solvent was evaporated at reduced pressure, and the solution taken up in 1 liter of dimethoxyethane.

75 G of the sodium salt of taurine and 1.5 g of potassium iodide were added, after which the mixture was left under agitation at ambient temperature for 120 hours and then evaporated under reduced pressure. 100 Ml of pyridine were added, the mixture diluted with 300 ml of ethanol and the solid obtained was filtered off. By recrystallising from methanol, the product was obtained having a m.p. of 179°–182° C., being identical to that obtained in Example 2.

The present invention also provides the taurine derivative N,N-di(acetylsalicyloyloxy ethyl)taurine (also referred to herein as "AST"), and its pharmaceutically acceptable salts with alkali metals, alkaline earth metals and organic basic substances.

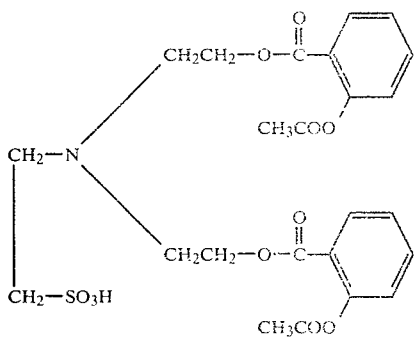

AST is of the formula and exhibits unexpectedly useful anti-inflammatory, anaegesic and antipyretic activity. The present invention therefore further provides pharmaceutical compositions which contain AST or a salt thereof, together with a pharmaceutically acceptable carrier or diluent, for the treatment of rheumatic conditions, arthritis, arthrosia, neuralgia, fever and similar conditions.

The compound AST may be prepared by reacting diethanoltaurine with an active functional derivative of acetylsalicylic acid, such as the halide, ester or mixed anhydride, as shown by the equation:

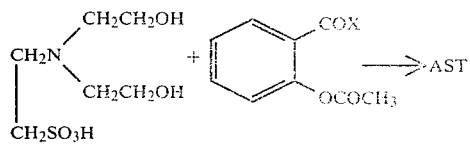

in which X is an active group, such as halogen, a residue capable of forming a mixed anhydride, for instance an ethoxycarbonyloxy radical or similar activating group. In the simplest case, when the acid chloride of acetylsalicylic acid is used, the reaction is advantageously carried out in the presence of an acid acceptor, for instance an organic tertiary base such as pyridine or triethylamine, which may be also act as a solvent. The AST salts can readily be converted to the free acid conventional procedures, and vice versa.

Synthesis of N,N-di(acetylsalicyloyloxyethyl) taurine, AST

Acetylsalicyloyl chloride was added gradually to 35.7 g of stirred diethanoltaurine in 350 ml of anhydrous pyridine at room temperature until the reaction mixture became brown (80 g). After a further hour with stirring the reaction mixture was diluted with 2 liters of ethanol and cooled in a refrigerator. The product of salmon color which crystallized was filtered off and repeatedly recrystallized from acetone (or ethanol) until the salmon color which accompanied the original precipitate had disappeared. 40 g of N,N-di(acetylasalicyloyloxyethyl) taurine, m.p. 185°–188° C., were thus produced.

Properties of N,N-di(acetylsalicyloyloxyethyl) taurine, AST

Elemental analysis found: C 53.75% Theory: C 53.64%. H 5.08% Theory: H 5.02%. N 2.60% Theory: N 2.61%.

M.p. 185°–188° C.

N.M.R. in $C_5D_5N/D_2O$: δ2.60 (s, $CH_3COO-$); 3.03 (t, J=6 Hz, $-N(CH_2-)_2$); 3.43 (s, $-SCH_2CH_2N-$); 4.42 (t, J=6 Hz, $-CH_2O-$), 7–8 (m, ArH).

IR in Nujol, Registered Trade Mark $\lambda_{max}$ 2800, 1750, 1715, 1600, 1450, 1370, 1250, 1185, 1170, 1080, 1020, 910, 740 cm$^{-1}$.

In pharmaco-toxicological tests on laboratory animnals, AST showed marked antiinflammatory, analgesic and antipyretic properties comparable to those of acetylsalicylic acid. In addition, in comparison with the latter, the tested product was less toxic, did not exert any appreciable gastric injury and showed a more prolonged pharmacodynamic activity.

These properties are illustrated in more detail as follows:

ACUTE TOXICITY

Tests were carried out both on mice and rats by means of oral, subcutaneous, intraperitoneal and intravenous administration.

In the case of oral administration, the product was used in the acid form suspended in an aqueous solution of carboxymethylcellulose, whilst in the case of parenteral administration it was made soluble by salt formation with sodium hydroxide in a physiological solution with a neutral final pH.

The results are given in the following table, together with the results found in the literature for acetylsalicylic acid (ASA).

Wherever possible, the values of the $LD_{50}$ were calculated using the probit method; if no mortality took place even at very high dosages, the maximum dosage tested has been given.

| Species of Animal | Administration | $LD_{50}$ (mg/kg) AST | ASA |
|---|---|---|---|
| Mouse | Oral | 5,000 | 1,050 |
| Mouse | Subcutaneous | 2,000 | — |
| Mouse | Intraperitoneal | 1,300 | 420 |
| Mouse | Intravenous | 520 | — |
| Rat | Intravenous | 530 | — |

GASTRO-INTESTINAL TOLERABILITY

Rats which had not been fed for 24 hours were used. The AST product was administered orally as the acid or the sodium salt at a dosage of 335 mg/Kg suspended in 1% carboxymethylcellulose. On a molar basis this dosage is equivalent to a dosage of acetylsalicylic acid which had repeatedly been found to cause gastric ulcers, i.e. 225 mg/Kg of acetylsalicylic acid. Both the methods of treatment and the observation time were identical for the 3 groups of animals. Result: Whilst the rats treated with acetylsalycylic acid showed 5 to 10 haemorrhagic gastric ulcers, the rats treated with either form of the present compound did not show any alteration of the gastric or intestinal mucosa.

ANALGESIC ACTIVITY (A) Test of convulsions produced by phenylquinone injected into mice by the intraperitoneal route. The AST product was administered orally both in the acid form (AST Ac) and as the sodium salt (AST Na). It was compared with a molar equivalent dosage of acetylsalicylic acid and with a carboxymethylcellulose placebo. The convulsions were induced at varying intervals from the oral treatment counting from the first 20 minutes after the injection of phenylquinone.

| Product and form | Dose (mg/Kg) | Inhibition % of convulsions in respect of treatment with placebo | | |
|---|---|---|---|---|
| | | 1h | 2h | 4h |
| ASA | 200 | 23 | 37 | 17 |
| AST Ac | 300 | 10 | 11 | 0 |
| AST Na | 300 | 56 | 87 | 46 |

(B) Mechanical pressure test on inflamed rat's paw. The AST product was administered both in the acid and sodium salt form by the oral method. It was compared with a molar equivalent dosage of acetylsalicylic acid and with a carboxymethylcellulose placebo. The inflammation of the paw was induced by a local injection of yeast simultaneously with the oral treatment with the drugs and the tenderness was measured in grams of mechanical pressure required to cause a reaction in the animal.

| Product and form | Dose (mg/Kg) | % Inhibition of the hyperalgesia in respect of treatment with placebo | | |
|---|---|---|---|---|
| | | 1h | 3h | 5h |
| ASA | 200 | 27 | 1 | 0 |
| AST Ac | 300 | 47 | 47 | 19 |
| AST Na | 300 | 64 | 33 | 30 |

ACTIVITY AGAINST EDEMA (A) Edema resulting from yeast in the paw of the rat. The AST product was administered orally both in the acid and sodium salt form. It was compared with a molar equivalent dose of acetylsalicylic acid and with carboxymethylcellulose placebo. The edema of the paw was induced with a local injection of the yeast simultaneously with the oral treatment with the drugs, and the volume of the paw was measured in hundredths of milliliter.

| Product and form | Dose (mg/Kg) | Inhibition of the edema with respect to treatment with placebo | | |
|---|---|---|---|---|
| | | 1h | 3h | 5h |
| ASA | 200 | 41 | 51 | 55 |
| AST Ac | 300 | 42 | 38 | 48 |
| AST Na | 300 | 39 | 38 | 50 |

(B) Edema as a result of nystatin in the rat's paw. The long duration of this type of edema enabled the animals to be repeatedly treated in order to ascertain the presence if any of the protracted effect of the AST product also using parenteral administration. The comparison was carried out using a molar equivalent dose of acetylsalicylic acid administrated orally and with the carboxymethylcellulose placebo also only administered orally. The AST product was used in the acid form orally and in the salt form using intraperitoneal administration.

The dosages of the drugs, always proportional to one another, were varied from day to day, i.e.: the first day a dosage of 200 mg/Kg of ASA and 300 mg/Kg of AST; the second day a double dose of each; the third day a double dose of each divided into two equal components administered with a spacing of 9 hours (10 am and 7 pm respectively); the fourth day no treatment in order to check the length of the effect after the fourth administration.

The anti-edema agent was injected into the paw on the night before the first treatment with the drugs and the volume of the paw was measured in hundredths of milliliter.

| Product and form | Method of Administration | Dose (mg/Kg) | % Inhibition of the edema in respect of treatment with placebo | | |
|---|---|---|---|---|---|
| 1st day of Edema | | | Times of the 1st dose | | |
| | | | 2h | 4h | 8h |
| ASA | p.o. | 200 | 8 | 10 | 7 |
| AST Ac | p.o. | 300 | 0 | 3 | 3 |
| AST Na | i.p. | 300 | 6 | 6 | 2 |
| 2nd Day of Edema | | | Times of the 2nd dose | | |
| | | | 2h | 4h | 8h |
| ASA | p.o. | 400 | 10 | 11 | 15 |
| AST Ac | p.o. | 600 | 3 | 2 | 10 |
| AST Na | i.p. | 600 | 11 | 17 | 18 |
| 3rd Day of Edema | | | Times of 3rd dose | | |
| | | | 2h | 4h | 8h |
| ASA | p.o. | 200 | 8 | 11 | 14 |
| AST Ac | p.o. | 300 | 8 | 7 | 6 |
| AST Na | i.p. | 300 | 14 | 17 | 16 |
| 4th Day of Edema | | | Times of 4th dose | | |
| | | | 13h | 17h | 23h |
| ASA | p.o. | 200 | 9 | 12 | 8 |
| AST Ac | p.o. | 300 | 3 | 3 | 0 |
| AST Na | i.p. | 300 | 12 | 16 | 11 |

ANTIPYRETIC ACTIVITY

Pyrexia from subcutaneous yeast in the rat. The AST product was administered orally in the acid from and the salt form with sodium, and by the intraperitoneal method in the salt form. It was compared with a molar equivalent dose of acetylsalicylic acid administered orally and with a carboxymethylcellulose placebo. The pyrexia was induced with a subcutaneous injection of yeast on the evening prior to the drug treatment, i.e. 16 hours before.

| Product and form | Method of Administration | Dose (mg/Kg) | % Inhibition of the pyrexia in respect of treatment with placebo | | | | |
|---|---|---|---|---|---|---|---|
| | | | 1h | 2h | 4h | 6h | 8h |
| ASA | p.o. | 200 | 78 | 103 | 114 | 58 | 45 |
| AST Ac | p.o. | 300 | 18 | 26 | 30 | 25 | 9 |
| AST Na | p.o. | 300 | 8 | 0 | 0 | 0 | 0 |

| Product and form | Method of Administration | Dose (mg/Kg) | % Inhibition of the pyrexia in respect of treatment with placebo | | | | |
|---|---|---|---|---|---|---|---|
| AST Na | i.p. | 300 | 65 | 75 | 56 | 50 | 69 |

The present compound is highly advantageous for the treatment of inflammatory, pain, fever and more generally as an antirheumatic agent. Pharmaceutical compositions for oral or parenteral use may be made up for administration using conventional procedures. For instance, tablets may be prepared which contain 0.5–1.5 g of AST-Na with known excipients conventionally used in the art or vials containing 0.3–1.2 g of AST-Na in twice-distilled sterile water.

What is claimed is:

1. A taurine derivative of general formula (I):

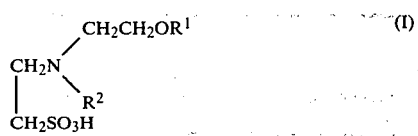

wherein $R^1$ is selected from the group consisting of nicotinoyl, 3,4,5-trimethoxybenzoyl and acetylsalicyloyl groups and $R^2$ is selected from the group consisting of $R^1$ as defined and $-CH_2CH_2OR^1$ wherein $R^1$ is as defined hereinabove; and pharmaceutically acceptable salts thereof.

2. N-nicotinoyl-N-(2-nicotinoyloxy)ethyltaurine.

3. N,N-di-[2-(3,4,5-trimethoxybenxoyloxy)ethyl]taurine.

4. N,N-di(acetylsalicyloyl-oxyethyl)taurine and a pharmaceutically acceptable salt thereof.

5. A pharmaceutical composition with antilipemic activity, said composition containing an effective amount of a taurine derivative of the general formula (I)

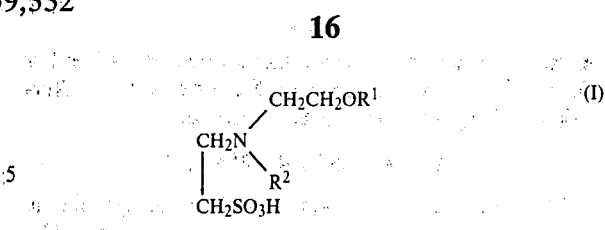

in which $R^1$ is nicotinoyl or 3,4,5-trimethoxybenxoyloxy or a salt thereof, together with a pharmaceutically acceptable carrier or diluent.

6. A pharmaceutical composition with choleretic activity, said composition containing an effective amount of a taurine derivative of the general formula (I)

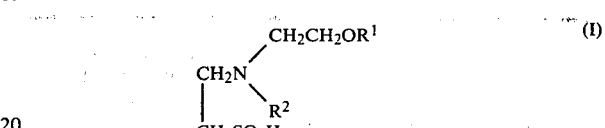

in which $R^1$ is nicotinoyl or 3,4,5-trimethoxybenxoyloxy or a salt thereof, together with a pharmaceutically acceptable carrier or diluent.

7. A pharmaceutical composition useful as an anti-inflammatory, analgesic and antipyretic agent containing an effective amount of N,N-di(acetylsalicyloyl-oxyethyl)taurine or a pharmaceutically acceptable salt thereof, together with a pharmaceutically acceptable carrier or diluent.

8. A method of treating hyperlipaemia, hypercholesterolaemia or inflammation, pain and pyrexia which consists essentially of administering an effective amount of a taurine derivative of the general formula (I)

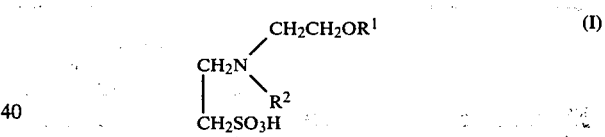

or a salt thereof, to a living host in need of such a treatment.

* * * * *